United States Patent [19]
Prutchi et al.

[11] Patent Number: 5,735,880
[45] Date of Patent: Apr. 7, 1998

[54] METHOD AND APPARATUS FOR RELIABLY PRODUCING PACING PULSE TRAINS

[75] Inventors: David Prutchi; Patrick J. Paul, both of Lake Jackson, Tex.

[73] Assignee: Sulzer Intermedics Inc., Angleton, Tex.

[21] Appl. No.: 714,388

[22] Filed: Sep. 16, 1996

[51] Int. Cl.⁶ ............................................. A61N 1/362
[52] U.S. Cl. .................................................. 607/9
[58] Field of Search ........................... 607/9, 10, 11, 607/29, 34

[56] References Cited

U.S. PATENT DOCUMENTS

| | | | |
|---|---|---|---|
| 3,518,997 | 7/1970 | Sessions | 607/34 |
| 3,845,773 | 11/1974 | Fontaine et al. | 607/9 |
| 3,866,614 | 2/1975 | Svensson | 607/9 |
| 4,031,899 | 6/1977 | Renirie | 607/34 |
| 4,140,132 | 2/1979 | Dahl | 128/419 |
| 4,688,573 | 8/1987 | Alt | 128/419 |
| 5,076,272 | 12/1991 | Ferek-Petric | 128/419 |
| 5,531,772 | 7/1996 | Prutchi | 607/17 |

*Primary Examiner*—William E. Kamm
*Attorney, Agent, or Firm*—John R. Merkling

[57] ABSTRACT

A method and apparatus for reliably producing a pulse train includes a control system which automatically selects a secondary pulse generator circuit when high frequency pulses are needed or whenever the use of alternating pulse generators would be desirable. This secondary pulse generator may be provided for other functions or it may be dedicated to providing alternate pulses, for example, to increase the frequency of the primary pulse generator without the loss of amplitude. This system may be useful for many purposes including implementing a noninvasive programmed stimulation operation or for providing antitachycardia arrhythmia therapy.

20 Claims, 2 Drawing Sheets and # METHOD AND APPARATUS FOR RELIABLY PRODUCING PACING PULSE TRAINS

FIELD OF OUR INVENTION

Our invention relates to cardiac pacemakers, and more particularly to cardiac pacemakers which are capable of reliably delivering pacing pulse trains of desired amplitude.

BACKGROUND OF OUR INVENTION

Implanted cardiac pacemakers are employed to assist patients suffering from severe bradycardia or chronotropic incompetence. A cardiac pacemaker captures the heart by delivering an electrical pulse to the myocardium of a selected heart chamber during an interval in the cardiac cycle in which the cardiac tissue is excitable. These electrical pulses cause depolarization of cardiac cells and consequently, contraction in the chamber, provided that the energy of the pacing pulse as delivered to the myocardium exceeds the threshold value.

Pacemakers may have a pre-defined pacing rate or pre-defined range of pacing rates. Other pacemakers may be rate responsive or rate adaptive in which case the pacing rate may be adjusted based on sensed physiological parameters. For example, when the patient is undergoing emotional or physical stress, the pacing rate may be increased to accommodate the enhanced biological demands.

The delivery of fast bursts of pacing pulses may be used for antitachycardia therapy or non-invasive programmed stimulation ("NIPS"). In antitachycardia therapy, a fast burst of pacing pulses can be used to capture a certain region of the heart in order to terminate an arrhythmia. In non-invasive programmed stimulation, a fast burst of pacing pulses may be generated in a clinical setting to produce a tachycardia arrhythmia for diagnostic purposes.

Delivery of such fast bursts of pacing pulses imposes a tremendous burden on the voltage multiplication and regulation circuits used to charge tank capacitors in typical pacemakers. This burden often makes it difficult to produce trains of closely separated pacing pulses with consistently high output amplitude. This burden is further increased as the internal impedance of the pacemaker battery increases with increased battery depletion.

When producing high frequency pulse trains, the tank capacitor from which the energy is delivered must be recharged fast enough between pulses to ensure that all the pulses in the train have consistently high output amplitude. This is necessary to ensure that the desired stimulation of the heart muscle is achieved.

Generating high frequency bursts, however, is problematic for typical pacemakers, and this is especially so for those designed to treat bradyarrhythmias. One reason for this is that the internal impedance of a typical lithium-iodide pacemaker battery is relatively high even when it is new. As the battery is depleted, its internal impedance increases to the point where the end of battery life is reached. In typical batteries the internal impedance of the battery may run from hundreds of ohms initially to hundreds of kiloohms near the end of battery life.

As a result of increasing battery impedance, the amount of charge that can be drawn within a given amount of time by the pacemaker's circuitry from the battery to fully recharge the tank capacitor decreases. Eventually, with sufficiently increased battery impedance and sufficiently high pulse frequency, not enough charge can be drawn from the battery to fully recharge the tank capacitor. As a result, the amplitude of pulses in the pulse train may be reduced beyond the point where reliable stimulation of heart muscle is achieved. Thus, the performance of the high frequency pacing therapy may be reduced or completely mitigated.

Consistently maintaining the desired pulse amplitude may be a problem at normal pacing rates when battery impedance is excessive. The same pulse amplitude problems that occur at higher frequency can occur at lower frequencies because the battery impedance may be high enough that complete recharge of the tank capacitor can not be accomplished in the available time period for recharge.

If the amplitude of the pacing pulses is sufficiently diminished, it is possible that the pacing pulses will not capture the heart muscle. This could have severe effects on the patient.

Therefore, it would be highly desirable to provide a system which enables pulses to be reliably produced with consistently appropriate amplitude.

SUMMARY OF OUR INVENTION

We have invented an implantable pacemaker that is capable of reliably producing pulse trains of consistently appropriate amplitude. The pacemaker uses two pulse generators which operate in alternate cycles to allow recharging of each pulse generator tank capacitor while the other tank capacitor is being discharged. In this way a pulse is provided alternately by each of the pulse generators. The tank capacitor of each pulse generator therefore has effectively almost twice the recharge time. As a result, even when the impedance of the battery is substantially increased as a result of the approach of end of battery life, pulses of consistently high voltage amplitude may be produced because of the additional time available to recharge the capacitors.

In many instances, it is advantageous to provide an additional pulse generator to implement the present invention. However, there are some instances where at least two pulse generators are already used. In such cases, the second pulse generator would not conventionally have been used to produce the pulse trains. For example, in a dual chamber stimulator, one of a pair of pulse generators may provide ventricular stimulation while the other provides atrial stimulation. In accordance with the present invention, the second pulse generator may be co-opted into providing alternate pulses when necessary.

Where two pulse generating systems are utilized to provide pulse trains that maintain the desired pulse amplitude, it is advantageous to have a way to automatically enable the cycling between the first and second pulse generators on alternate cycles. Whenever necessary, the pacemaker includes circuitry to perform automatic source toggling between the primary tank capacitor and an additional tank capacitor for generating successive pacing pulses in the train. In this way, while one of the capacitors is being used to deliver a pacing pulse, the other is being recharged.

DETAILED DESCRIPTION OF OUR PREFERRED EMBODIMENT

We will now describe the preferred embodiment of our invention with reference to the accompanying figures. Like numerals will be used to designate like parts throughout.

Figure 1:
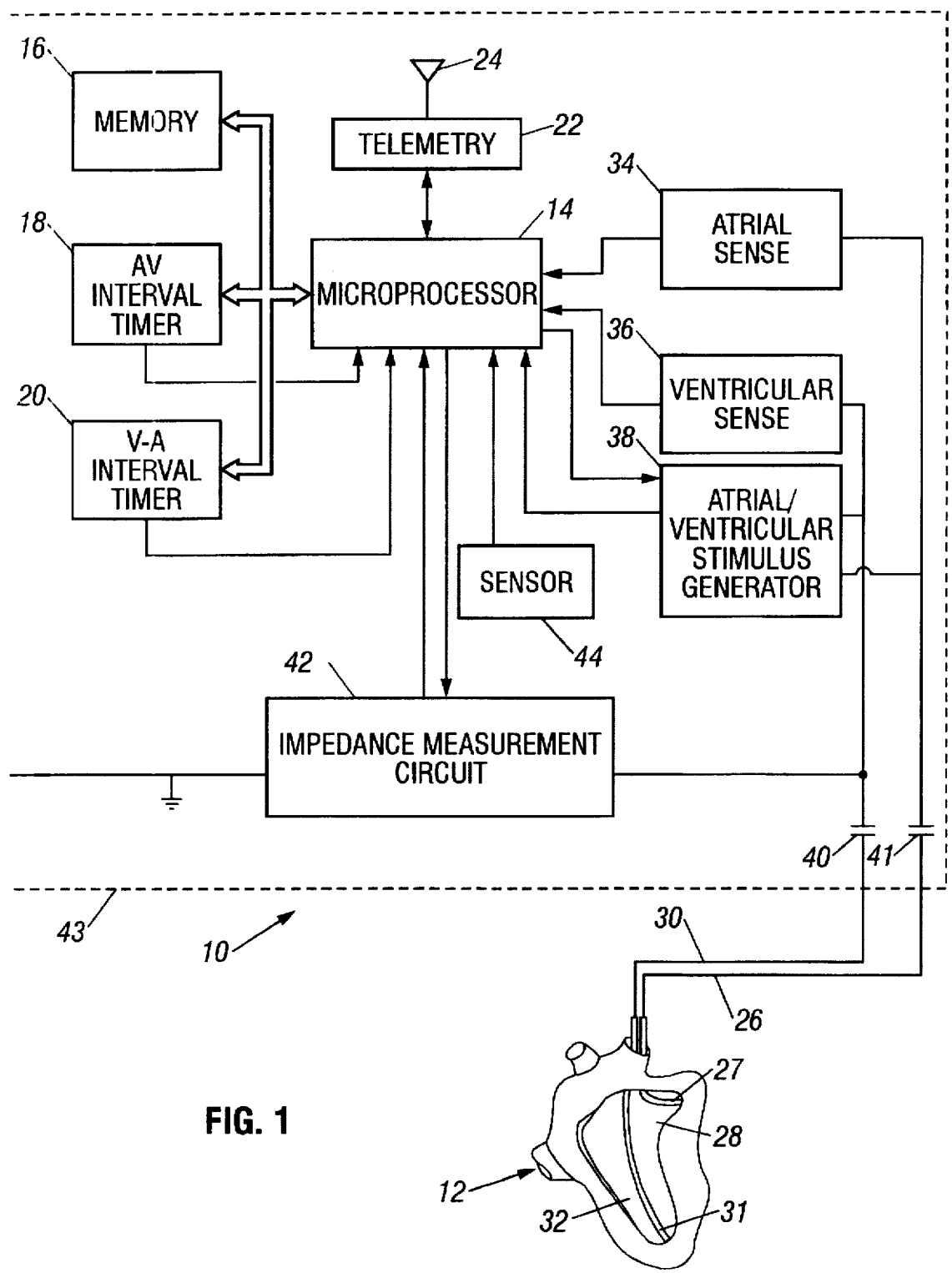
FIG. 1 is a block diagram of an embodiment of a pacemaker according to our invention.

Referring now to FIG. 1, an implantable pacemaker, generally designated 10, is illustrated in schematic fashion with connection to the human heart 12. The present invention is applicable to pacemakers with atrial sensing, ventricular sensing, ventricular pacing and atrial pacing or any combination thereof. In addition, the features of our invention could also be combined with an implantable defibrillator/cardioverter.

With this understanding, the illustrated pacemaker 10 comprises a microprocessor 14 which executes various control programs to regulate the action of the pacemaker. The microprocessor 14 may be connected to additional memory 16 which stores programs and data as needed. Conventionally, one or more internal clocks may be provided to permit timing of various events. For example, an A-V interval timer 18 may be provided. Similarly, a V-A interval timer 20 may also be provided as known in the art.

The microprocessor may also be provided with a telemetry circuit 22 to enable communication by the antenna 24 with an external pacemaker programmer (not shown). Telemetry permits an attending physician to obtain data and information from the pacemaker and to control the pacemaker by setting various selectable parameters.

Our invention is amenable to implementation with pacemakers using either bipolar or unipolar leads. The illustrated pacemaker 10 may be connected to the heart 12 through a first lead 26 to an electrode 27 in the atrium and through a second lead 30 to an electrode 31 in the ventricle 32. An indifferent electrode (e.g. the pacemaker can) is provided to complete the electrical circuit through the body. In the illustrated embodiment, a can 43 or outer casing of the pacemaker serves as the indifferent electrode.

Atrial electrogram sensing, through an atrial sense circuit 34, and ventricular sensing through a ventricular sense circuit 36, provide information to the microprocessor 14 concerning the condition and responsiveness of the heart. In addition, pacing pulses are provided to the ventricle and/or the atrium from the atrial/ventricular stimulus generator 38.. However, it is clearly with the scope of those skilled in the art to provide cardioversion/defibrillation capabilities in response to the detected condition of the heart.

Stimulation of the heart is passed through coupling capacitors 40 and 41 in a conventional fashion. The switches 73 and 74 and resistors 75 and 76 may be used to actively discharge the coupling capacitors 40 and 41.

To control the pulse rate of the ventricular stimulus generator 38, the microprocessor may acquire information on the condition of the heart through an impedance circuit 42. The impedance circuit 42 detects changes in impedance primarily due to the changing shape of the heart, which may be related to the physical shape of the heart as it beats and pumps blood. This information can be used to derive a measure of the stroke volume or ejection fraction or end diastolic volume of the heart. Furthermore, the shape of the impedance waveform can provide further information on other cardiac timing parameters such as isovolumetric contraction time or pre-ejection period. One exemplary impedance circuit is described in U.S. Pat. No. 5,531,772 to Prutchi, which is expressly incorporated by reference herein.

In addition to the measurement of impedance, a sensor 44 may also be provided to obtain an indication of physiologic need and adjust the pacing rate. Such a sensor may be an accelerometer, as described by Dahl, U.S. Pat. No. 4,140,132, a temperature sensor as described Alt, U.S. Pat. No. 4,688,573, or any other suitable sensor parameter which may be correlated to physiological need of the patient.

Figure 2:
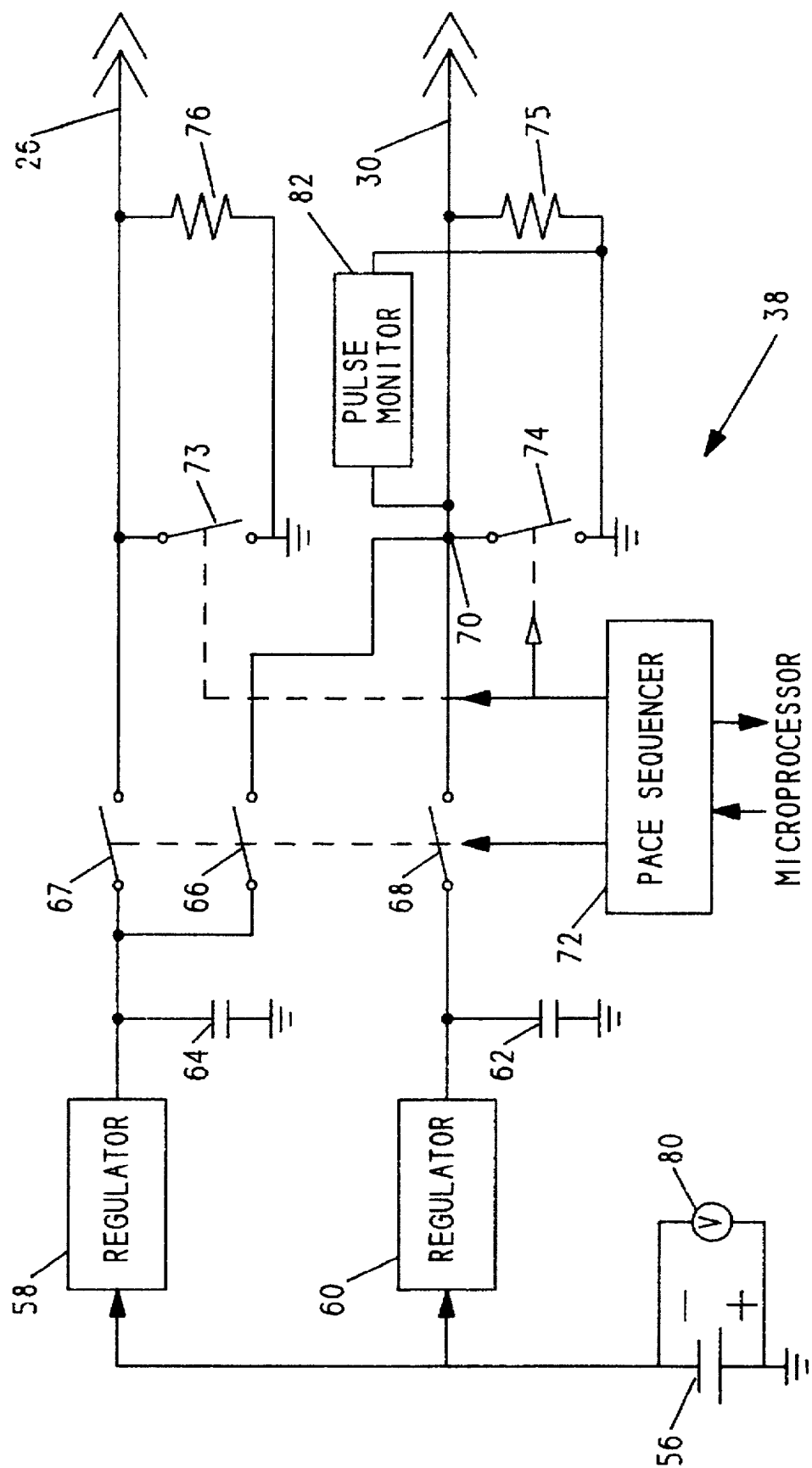
FIG. 2 is a circuit diagram of an embodiment of a pulse generator for reliably producing trains that maintain a desired pulse amplitude.

The atrial/ventricular stimulus generator 38, shown in FIG. 2, includes a battery 56 connected to a pair of regulators 58 and 60. The regulator 60 is connected to a tank capacitor 62 while the regulator 58 is connected to a tank capacitor 64. The regulators 58 and 60 include multiplication and regulation circuitry used to charge the tank capacitors 62 and 64.

The tank capacitor 64 is connectable by a switch 66 to a node 70 while the regulator 60 is connected by a switch 68 to the same node 70, which connects via the lead 30 to the ventricle 32 of the heart 12. The tank capacitor 64 is also connectable via the switch 67 and the lead 26 to the atrium 28 of the heart 12.

The pace sequencer 72 controls the switches 66, 67 and 68 to utilize the regulator 58 and tank capacitor 64 to augment the pulses produced by the regulator 60 and tank capacitor 62 when needed. In particular with the switch 66 open and the switch 68 closed, a normal pacing pulse may be produced by the tank capacitor 62 to ventricle 32.

At the same time with switch 67 closed, a pulse train may be delivered via the lead 26 to the atrium 28. After each pulse is created, and transmitted to the heart tissue 12, the switches 67 and 68 may be opened allowing the capacitors 62 and 64 to be recharged by the regulators 58 and 60 and battery 56.

When it is desired to augment the ventricular pacing pulse train, the switch 67 is opened and the switches 66 and 68 may be alternately opened and closed at a desired frequency by the pace sequencer 72. This allows additional time for the capacitors 62 and 64 to be recharged. Namely, while the capacitor 64 is being discharged to produce a pacing pulse, the capacitor 62 may be recharging and vice versa.

The pace sequencer 72 may be a state machine which is programmed to provide switching sequences. The sequencer 72 is connected for control by the microprocessor 14. However, a variety of other conventional techniques may be used to control the switches 66,67,68,73 and 74.

With the present invention it is possible to produce a normal pulse frequency through the regulator 60 and capacitor 62 and then when selected, produce a higher frequency pulse train without concern for loss of reliability. Because of the extra time provided for recharging of the tank capacitors 62 and 64, the possibility of incomplete charging is lessened and therefore the likelihood that pulses of full amplitude will be produced is increased.

As one example of the application of the present invention, the regulator 60 and capacitor 82 can produce normal frequency pacing pulses. When it is desired to undergo a noninvasive programmed stimulation cycle, one or more bursts of high frequency pulses may be produced for ventricular analysis and diagnostic purposes. This may be done by alternately producing pulses using regulator 60 and capacitor 62 and the regulator 58 and capacitor 64. This stimulation cycle can be implemented through telemetry by the physician. A signal received by the antenna 24 and telemetry circuit 22 may be passed to the microprocessor 14 which in turn sends an appropriate control signal to the sequencer 72. In the same way the stimulation may be terminated when sufficient data has been obtained.

Similarly, it may be desirable to counteract a detected tachycardia arrhythmia by producing a high frequency burst cycle. A tachyarrhythmia is detected by the atrial sensor circuit 34 or the ventricular sense circuit 36. The microprocessor 14 then signals the pace sequencer 72 to implement a high frequency burst cycle to the ventricle using both tank capacitors 62 and 64. Once the arrhythmia has been countered, the pace sequencer 72 may automatically revert to a normal pacing frequency.

In accordance with still another embodiment of the present invention, tank capacitors 62 and 64 are used to produce a combined pulse train when low battery condition is detected by the conventional monitor 80 or low pulse amplitude has been detected by a monitor 82. That is, upon detection of a low battery or low pulse amplitude, the microprocessor 14 directs an appropriate control signal to the sequencer 72 to operate switches 66 and 67 to co-opt the regulator 58 and tank capacitor 64 to produce alternate pulses of a pulse train supplied to the lead 30.

The monitor 82 may be implemented as disclosed in a copending application, by the same inventors, filed on the same date as this application, titled "Method and Apparatus for Detecting Amplitude Loss in Cardiac Pacing Pulses", which is hereby expressly incorporated by reference herein.

Our invention may be embodied in other specific forms without departing from the spirit or central characteristics thereof. The foregoing description is, therefore, to be viewed in all respects all illustrative and not restrictive. The scope of our invention is defined solely by the appended claims.

We claim as our invention:

1. A cardiac stimulation apparatus for a patient whose heart needs cardiac therapy comprising:

a capacitor charging circuit; a first capacitor electrically connected to said capacitor charging circuit for providing a pacing pulse;

a second capacitor electrically connected to said capacitor charging circuit for providing a pacing pulse; and a control circuit for enabling at least one of said capacitors to be charged and discharged, said control circuit connected to a sequencer for enabling said first and second capacitors to be charged and discharged in alternate cycles to produce a pulse train formed by pulses from said first and second capacitors.

2. The apparatus of claim 1 further comprising means for connecting both of said capacitors to the ventricle.

3. The apparatus of claim 1 including a detector connected to said control circuit for detecting battery end of life conditions, said sequencer being activated by said control circuit when battery end of life conditions are detected.

4. The apparatus of claim 1 wherein said sequencer is activated by said control circuit to produce higher frequency pulse trains at a selected voltage than could be created using only said first capacitor.

5. The apparatus of claim 1 wherein said capacitor charging circuit further comprises a first capacitor charging circuit for charging said first capacitor and a second capacitor charging circuit for charging said second capacitor.

6. The apparatus of claim 5 further comprising means for connecting said first capacitor to the ventricle and means for connecting said second capacitor to the atrium, and wherein said sequencer further comprises a first switched connection between said first and second capacitors and a second switched connection between said second capacitor and said means for connecting said second capacitor to the atrium.

7. The apparatus of claim 1 including means for detecting tachycardia arrhythmia connected to said control circuit, said control circuit activating said sequencer in response to the detection of a tachycardia arrhythmia.

8. The apparatus of claim 1, including a telemetry device connected to said control circuit for receiving a signal for activating said sequencer.

9. The apparatus of claim 1 further comprising means for detecting a predetermined condition and wherein said control circuit, in response to said means for detecting a condition, causes said second capacitor to produce alternate pulses with said first capacitor.

10. A method for cardiac stimulation comprising the steps of:

producing a pulse train for cardiac stimulation, at least part of said pulse train comprising pulses powered from a first tank capacitor alternating with pulses powered from a second tank capacitor;

applying said pulse train to the heart of a patient; and recharging one of said tank capacitors while the other of said tank capacitors is being discharged.

11. The method of claim 10, including the steps of providing a battery to supply electrical power to said first and second capacitors;

monitoring a condition of said battery;

detecting a low battery condition; and producing said pulse train using said first and second tank capacitors when said low battery condition is detected.

12. The method of claim 10 including the step of detecting a tachycardia arrhythmia and producing said pulse train using said first and second capacitors in response to the detection of a tachycardia arrhythmia.

13. The method of claim 10 including the steps of providing an implantable pacemaker capable of performing the method of claim 10;

sending a signal to said pacemaker, producing said pulse train using pulses produced by said first and second tank capacitors in response to the receipt by said pacemaker of said signal.

14. The method of claim 10 including the step of monitoring the amplitude of the pulses of said pulse train and producing said part of said pulse train comprising pulses powered from said first tank capacitor alternating with pulses powered from said second tank capacitor when low pulse amplitude is detected in said monitoring step.

15. The method of claim 10 including the step of producing said part of said pulse train at a selected pulse voltage using said first and second capacitors at a higher frequency than could be produced using only said first capacitor.

16. The method of claim 10 including the steps of using said second tank capacitor to produce pulses and supplying said pulses to the atrium, and selectively adding said pulses supplied by said second capacitor to said pulse train and supplying said pulse train to the ventricle.

17. The method of claim 10 including the steps of:

providing a battery;

regulating and multiplying potential received from said battery and wherein said recharging step comprises supplying that regulated and multiplied potential to said first tank capacitor.

18. The method of claim 17 including the steps of separately regulating and multiplying the potential received from said battery and supplying that regulated and multiplied potential to said second tank capacitor.

19. The method of claim 10 including the step of implementing non-invasive programmed stimulation using said second tank capacitor to produce alternate pulses in said pulse train.

20. The method of claim 10 including the step of automatically producing alternating pulses by discharging said second tank capacitor when a certain condition is sensed.

* * * * *